United States Patent
Mirza et al.

(10) Patent No.: US 6,485,758 B2
(45) Date of Patent: Nov. 26, 2002

(54) HANGOVER TREATMENT

(75) Inventors: M. Ather Mirza, St. James, NY (US); Romi Mirza, St. James, NY (US); James R. Brennan, Setauket, NY (US)

(73) Assignee: Vasolabs, Inc., Smithtown, NY (US)

( * ) Notice: Subject to any disclaimer, the term of this patent is extended or adjusted under 35 U.S.C. 154(b) by 74 days.

(21) Appl. No.: 09/788,903

(22) Filed: Feb. 20, 2001

(65) Prior Publication Data

US 2001/0043956 A1 Nov. 22, 2001

(Under 37 CFR 1.47)

Related U.S. Application Data

(60) Provisional application No. 60/183,511, filed on Feb. 18, 2000.

(51) Int. Cl.⁷ ................................................ A01N 65/00
(52) U.S. Cl. .................... 424/725; 424/125; 424/725.1; 562/416; 514/89; 514/653; 546/301
(58) Field of Search ............................. 424/725.1, 725, 424/125; 502/416; 546/301; 514/89, 653

(56) References Cited

U.S. PATENT DOCUMENTS 6,399,116 B1 * 6/2002 Xiu 6,420,350 B1 * 7/2002 Fleischner

* cited by examiner

Primary Examiner—Leon B. Lankford, Jr.
(74) Attorney, Agent, or Firm—Collard & Roe, P.C.

(57) ABSTRACT

A cure for a hangover containing the active ingredient ephedrine in powdered form enclosed in a capsule. In a second embodiment this cure contains ephedrine and charcoal, while in a third embodiment, this cure contains Ephedra, charcoal and Vitamin B6. The use of any one of the three embodiments reduces the symptoms associated with alcohol intoxication and hangovers thereby speeding up recovery. The Ephedra, Vitamin B-6 and charcoal may be combined on a wt % ratio of 1:2.5:10. The Ephedra may come in the form of Ma Huang having 6% wt % Ephedra. One type of dosage is in the form of individual capsules having 10 Mg of Ephedra, 25 Mg of Vitamin B-6 and 100 Mg of activated charcoal. The recommended dosage would be two capsules so that users who are experiencing a hangover or alcohol related side effects may take up to 20 Mg of Ephedra, 50 Mg of Vitamin B-6 and 200 Mg of activated charcoal. This cure may also consist of a therapeutic method for curing the effects of alcohol consumption wherein this dosage could be taken after the consumption of alcohol.

13 Claims, No Drawings

HANGOVER TREATMENT

CROSS REFERENCE TO RELATED APPLICATIONS

The application claims the benefit of the filing date of copending Provisional Application Ser. No. 60/183,511, filed Feb. 18, 2000.

BACKGROUND OF THE INVENTION

The invention relates to a hangover cure that is designed to speed the time for recovery for an individual after they have ingested large quantities of alcohol. The term "alcohol" as used herein refers to ethyl alcohol and "alcoholic beverages" and refers to popular spirits or blends that are intended for human consumption. Alcohol intoxication spans a range of blood-ethanol concentrations from 50mg % at which some impairment of judgment occurs above 400mg %, which is associated with profound depression of vital physiologic functions, all the way to 600 mg % which leads to death.

Approximately 11 million youths under the age of 21 drink alcohol in the United States. According to the National Institute on Drug Abuse and the National Institute on Alcohol Abuse and Alcoholism in 1995, a total of $166,543 million was spent in the US on alcohol related matters. For example there was $77,150 million spent due to illness. In addition, there was $34,921 million spent in lost earnings of premature death, $24,752 million spent due to crashes fires and criminal justice, $15,830 spent on medical consequences from drinking, $7,231 lost because of crime, and $6,660 million spent because of specialty drug and alcohol services for Americans.

The symptoms of a hangover are headache, dehydration, congestion, stomach pains, and diarrhea. The hangover is caused by the breakdown of alcohol in the liver especially acetaldehyde which has been found to be highly toxic. Alcoholic beverages themselves have toxins called congers, which are the byproducts of fermentation and distillation.

SUMMARY OF THE INVENTION

The invention relates to a hangover cure that is designed to speed the time for recovery from a hangover for an individual after they have ingested large quantities of alcohol. In a first embodiment, this hangover cure contains Ephedrine, in a second embodiment, this cure contains Ephedrine and charcoal, and in a third embodiment, this cure contains Ephedrine, charcoal and Vitamin B6. The Ephedrine in the hangover cure is designed to act as a vasoconstrictor decreasing the size of the blood vessels while simultaneously acting as a stimulant and as a bronchiodilator.

This invention also includes a therapeutic method for relieving the side effects of alcohol consumption by a person which comprises administering to this person a composition consisting essentially of at least about 100 Mg of Ma Huang, at least about 50 Mg of charcoal and at least about 10 Mg of Vitamin B-6 in a dosage unit.

However, this method is preferably conducted after the user consumes alcohol and then receives a dosage unit comprising between 100 and 334 Mg of Ma Huang, 50 and 200 Mg of Charcoal, and 10–50 Mg of Vitamin B-6.

This dosage unit could be ingested in a capsule form, in a pill form or in a liquid form.

DETAILED DESCRIPTION OF THE PREFERRED EMBODIMENTS

Essentially, the invention relates to a hangover cure for persons who have ingested alcohol. The alcohol functions as a vasodilator, which means that when it is added to the bloodstream, it causes a dilation effect on the blood vessels. When added to the alcohol rich blood system, Ephedra counteracts the effects of alcohol by acting as a vasoconstrictor thereby decreasing the size of the blood vessels, and relieving the perceived pressure on the brain.

Ephedrine, which is an extract of Ephedra, is the nonproprietary name for the chemical substance -2-methylamino-1-phenylpropanol-01 and while it is not regulated as a controlled substance under the Controlled Substances Act (CSA), it is listed as a chemical under that law. However, small doses of 1-ephedrine are available off the shelf. One of the most common forms is Ma Huang a Chinese herb sold over the counter in nutrition and Vitamin stores.

Ephedrine is used as a stimulant and a bronchodilator and is chemically similar to drugs in the amphetamine group. It functions as a main ingredient in legally available energizers, nutritional suppliments, and dietary teas. Essentially, Ephedrine triggers a mild burst of energy when ingested into the body. In addition to the stimulant effects, which can include feelings of alertness and reduced appetite, Ephedrine also relaxes bronchial muscles and dilates airways, and can cause an increase in blood pressure and heart rate. A synthetic form of the drug pseudoephedrine is found in over the counter and prescription cold and allergy products.

Charcoal is also used to help a person recover from a hangover because it functions as an adsorbent. Adsorbents are chemically inert powders that have the ability to adsorb gasses, toxins, and bacteria usually in the gastrointestinal tract. Charcoal is widely considered to be the emergency treatment of choice for virtually all drug and chemical poisoning.

The adsorptive properties of charcoal can be greatly increased by treating it with various substances such as steam, air, carbon dioxide, oxygen, zinc chloride, sulfuric acid or phosphoric acid or a combination of some other substances at a temperature ranging from 500 degrees Fahrenheit to 900 degrees Fahrenheit.

This treatment is commonly referred to as activation wherein the activating agent presumably removes substances previously adsorbed on the charcoal and, breaks down the granules of carbon into smaller ones having a greater surface area. For example, it has been estimated that one milliliter of charcoal has a surface area of 1000 $m^2$.

In addition to wood, many other substances can be used as a source for charcoal such as, sucrose, lactose, rice starch, coconut pericarp, bone, blood, various industrial wastes. The end product is a fine black odorless and tasteless powder that is free from gritty matter that is insoluble in water or other known solvents.

Furthermore, another supplement to this cure is Vitamin B6, also known as pyridoxine. This Vitamin is involved in the formation of body protein and structural compounds, chemical transmitters in the nervous system, red blood cells, and prostaglandins. In addition, Vitamin B6 is also important in maintaining hormonal balance and proper immune function.

Deficiency in Vitamin B6 is characterized by depression, convulsions, glucose intolerance, anemia, impaired nerve function, cracking of the lips and tongue and seborrhea or eczema. Those with the following health conditions: Asthma, premenstrual syndrome, carpal tunnel syndrome, depression, morning sickness, and kidney stones reported positive responses when they supplemented their diet with Vitamin B6.

Because Vitamin B6 is especially helpful in reducing nervous disorders, it forms a beneficial compliment to the effect of alcohol on the nervous system.

In the following examples, the indicated compositions are intended for three separate embodiments. These compositions could be taken in the form of a capsule, a pill, or other forms of ingestion such as a drink containing the active ingredients.

EXAMPLE 1

| | |
|---|---|
| Ma Huang (6 wt % Ephedra) | 334 Mg |
| Elcema G-250 Powder Cellulose | 54 Mg |
| Captex 300 | 8 Mg |
| Magnesium Stearate Lubricant | 2 Mg |
| Sipernat 50S | 2 Mg |

The first embodiment of the invention is a 400 mg capsule that contains 334 mg of Ma Huang extract containing 6 wt % Ephedra (approximately 20 mg of Ephedra), 54 mg of Elcema G-250 Powder Cellulose for binding, 8mg of Captex 300 to aid in the encapsulation, 2mg of Magnesium Stearate lubricant, and 2mg of Sipernat 50S as a flow aid. As stated above, the Ephedra functions as a vasoconstrictor counteracting the effects of alcohol in the bloodstream. In addition, because alcohol can also act as a depressant on the body, the stimulating quality of Ephedra also functions to counteract this side effect. Furthermore, since Ephedra acts as a decongestant, it also relieves the congestive symptoms commonly associated with hangovers.

EXAMPLE 2

| | |
|---|---|
| Ma Huang (6 wt % Ephedra extract) | 167 Mg |
| Charcoal | 100 Mg |
| Elcema G-250 Powder Cellulose for Binding | 46 Mg |
| Captex 300 | 8 Mg |
| Magnesium Stearate | 2 Mg |
| Sipernat 50S | 2 Mg |

The second embodiment of the invention is a 325 mg capsule that contains 167 mg of Ma Huang extract powder containing 6% Ephedra (approximately 10 mg of Ephedra), 100 mg of charcoal, 46 mg of Elcema G-250 Powder Cellulose for Binding, 8mg Captex 300 to aid in the encapsulation, 2mg of Magnesium Stearate Lubricant, and 2mg of Sipernat 50S as a flow aid. In this case, the addition of the charcoal allows this dosage to function with greater headache relief because the carbon in the charcoal acts as a detoxification agent by extracting impurities in the intestinal system from the introduction of alcohol moving them to the large intestine for removal. Furthermore, the addition of charcoal as an adsorbent in the digestive system will also relieve diarrhea, flatulance, and acidity in the stomach, symptoms that are common to most hangovers.

EXAMPLE 3

| | |
|---|---|
| Ma Huang (6 wt % Ephedra extract) | 167 Mg |
| Charcoal | 100 Mg |
| Vitamin B-6 (pyridoxine) | 25 Mg |
| Elcema G-250 Powder Cellulose for Binding | 46 Mg |
| Captex 300 | 8 Mg |

-continued
EXAMPLE 3

| | |
|---|---|
| Magnesium Stearate | 2 Mg |
| Sipernat 50S | 2 Mg |

A third embodiment of the invention is a 350 mg capsule that is similar to the second embodiment but contains an additional 25 mg of Vitamin B-6. In this case, the 25 mg of Vitamin B6 is added to the capsule so that when it is adsorbed into the bloodstream, it helps to counteract any harmful side effects of alcohol in the bloodstream. For example, alcohol functions as a diuretic depleting a person's body of water soluble vitamins and minerals. Thus, because Vitamin B-6 is water soluble, a person experiencing a hangover may have relatively low levels of Vitamin B-6. Therefore, by adding Vitamin B-6 or any other type of water soluble vitamin, a person may recover from a hangover at a faster rate.

All three of these embodiments are preferably presented in capsule form. In this way, the active ingredients of Ephedrine, charcoal and Vitamin B-6 can be presented in powder form to enter the bloodstream more rapidly. Once the capsule has been ingested, the gelatin outer coating breaks-down and the powdered active and non-toxic ingredients that break down within the digestive system of a person and enter their blood stream.

The solution shown in Example 3 was used in a double blind randomized parallel study comparing the test product in Example 3 to a placebo. Thirty four volunteers between the ages of 21 and 45 were invited to participate in the study. After signing a consent form and answering questions on a questionnaire relating to their demographic characteristics, drinking habits and state of health, the volunteers were entered into the study.

All of the volunteers followed the same procedure for the study. Volunteers reported at the study site which was a hotel and signed the consent form. These volunteers were then examined by a physician and vital signs were then taken. Upon approval to enter the study, a BAL reading was taken, and the volunteers were free to drink at an open bar, and partake of a food buffet. The bar was open until 2 A.M. on Saturday. At their discretion, volunteers went to their designated hotel room to sleep, after having vital signs taken, responding to a questionnaire relating to their symptoms, taking a physical sobriety exam administered by a physician, and taking a BAL test. They were instructed not to have any alcohol after leaving the study premises, and to report for breakfast the following morning at 8 A.M.

The following morning, the subjects were examined by a physician, wherein vital signs and BAL were taken. The subjects then answered a questionnaire relating to their symptoms.

Next, the study drugs were then administered wherein there were 2 capsules of the test drug or placebo used in a double blind fashion. The two different drugs were applied across a random group using the answers to the questionnaire to equalize the frequency of the active drug and the placebo with patients having similar answers on the questionnaire.

Volunteers were then asked to have breakfast wherein no caffinated foods or beverages were served. At periods of one and two hours after the initial exam, the volunteers repeated the original procedure consisting of an examination by the physician, a reading of vital signs and a blood alcohol level (BAL) reading. They then answered the same questionnaire relating to their symptoms. Thus, the data was available at a baseline test at approximately 8 A.M. when the test products were first given, and then at one and two hour intervals following the administration of the test products.

To determine the effects of the drugs repeated measures analysis of variance were performed on the percentage change in score from baseline at one and two hours after study products were administered. The baseline score was used to covariate. Each of the five questions on the questionnaire was scored from 1 to 3 with 1 equaling an absence of a symptom and 3 equaling a severe symptom. Thus, the total score for each participant could either equal 5 which is a complete absence of symptoms or 15 wherein all symptoms are severe.

The reported scores of the Active group receiving the dosage according to example 3, and the Placebo group receiving a placebo dosage are shown in Table 1 below.

TABLE 1

Demographic and Entry Characteristics of Study Population

| Heading | Active Group | Placebo Group |
|---|---|---|
| Number of Volunteers | 19 | 18 |
| Male | 9 | 8 |
| Female | 10 | 10 |
| Average Weight | 177 (108–320) | 172 (114–275) |
| Friday Night Results Average BAL (range) | 0.15 (0.065–0.311) | 0.14 (0.049–0.247) |
| Saturday AM Results | 8.42 (6–11) | 8.44 (6–11) |
| 9 A.M. Results Average Score | 6.89 (5–10) | 7.67 (5–9) |
| Average Ratio** | 0.788 (0.55–1.05) | 0.93 (0.63–1.29) |
| 10 A.M. Results Average Score | 6.32 (5–10) | 7.06 (5–10) |
| Average Ratio*** | 0.755 (0.5–1) | 0.859 (0.5–1) |

*This is a baseline reading.
**9 AM score/8 AM score
***10 AM score/8 AM score.

Based upon this test and the analysis of the results, the volunteers on the active product showed symptom improvement compared to the placebo.

Taking the value of 8.4 as the base measurement for both the active group and the placebo group, the best possible ratio for improvement would be 0.6 with the scores dropping to the minimum number 5. After ingesting either the active group or the placebo group, the active group participants showed a greater and faster recovery at 9AM (6.89 score and 0.788 ratio) than the placebo group (7.67 score and 0.93 ratio) with these scores taken from the average score of approximately 8.4 at 8AM. In addition, at 10 AM the active group participants also showed a greater and faster recovery (6.32 score and 0.755 ratio) than the placebo group (7.06 score and 0.859 ratio).

These scores were then analyzed using a statistical analysis to determine the significance of the improvement for the active group.

TABLE 2 shows the statistical analysis of the testing.

| Source | DF | Type I SS | Mean Square | F Value | Pr > F |
|---|---|---|---|---|---|
| Base | 1 | 0.51215028 | 0.51215028 | 66.83 | 0.0001 |
| Treat | 1 | 0.20907438 | 0.20907438 | 27.28 | 0.0001 |
| Sub (Treat) | 34 | 1.56336154 | 0.04598122 | 6.00 | 0.0001 |
| Time | 1 | 0.08406261 | 0.08406261 | 10.97 | 0.0022 |
| Treat Time | 1 | 0.00000035 | 0.00000035 | 0.00 | 0.9946 |

With this study, a statistical analysis was performed to determine the statistical significance of these values. A test result for the Active Group or the Placebo Group is statistically significant over the baseline if the P value is less than 0.05 ($p < 0.05$).

A repeated measures analysis of covariance (baseline score and weight as covariates) shows the improvement in the active group compared to the placebo group was significant ($p < 0.05$). The symptoms of the users improved in both treatment groups in the second hour, as time became a factor in the alleviation of symptoms. The ratios after one hour post dosage were also significantly different ($p < 0.05$) favoring the active treatment, based on an analysis of covariance. The second hour results favored the active treatment, but just missed statistical significance ($p < 0.08$).

In addition, looking at the individual scores, one hour after dosing, 9 of 19 (47%) of the volunteers showed greater than 50% improvement in the active group. In the placebo group 2 of 18 (11%) of the volunteers showed a similar improvement ($p = 0.2$), supporting the statistically significant difference in average results. More than 50% improvement in symptom score is more than twice as probable with the active product than with the placebo. Two hours after dosing, 13 of 19 (68%) of the volunteers showed greater than 50% improvement in the active group. In the placebo group only 7 of 18 volunteers (39%) showed a similar improvement.

Thus, it seems apparent that the administration of this third embodiment of the invention helps to alleviate the side effects associated with the consumption of alcohol.

Accordingly, while several embodiments of the present invention have been shown and described, it is to be understood that many changes and modifications may be made thereunto without departing from the spirit and scope of the invention.

What is claimed is:

1. A composition for relieving the side effects of alcohol consumption in humans comprising the following ingredients:
   a) a combination of active ingredients comprising:
      i) at least 0.01 wt % of charcoal;
      ii) at least 0.01 wt % of Vitamin B-6; and
      iii) at least 0.01 wt % of Ma Huang; and
   b) an inert, non-toxic carrier designed to bind said active ingredients together wherein said active ingredients in combination with said inert, non-toxic carrier ingredients total 100 wt % of the composition and wherein each wt % is based upon the total combined weight of the active ingredients and the inert non-toxic carrier.

2. The composition as claimed in claim 1, wherein said active ingredients in said composition comprise:
   at least 25 wt % of Ma Huang;
   at least 10 wt % of charcoal; and
   at least 1 wt % of Vitamin B-6.

3. The composition as claimed in claim 1, wherein said active ingredients comprise:
   at least 47 wt % Ma Huang;
   at least 25 wt % charcoal; and
   at least 7 wt % Vitamin B-6.

4. The composition as in claim 1, wherein said inert, non toxic ingredients comprise Elcema G-250 powder cellulose for binding; Captex 300; Magnesium Stearate; and Sipernat 50 S mineral oil lubricant.

5. A composition for relieving the side effects of alcohol consumption in humans comprising the following ingredients:
   at least 25 Mg of Ma Huang;
   at least 10 Mg of charcoal;
   at least 5 Mg of Vitamin B-6; and
   an inert non-toxic carrier designed to bind said active ingredients together wherein said active ingredients in combination with said inert, non toxic ingredients total 100 wt % of the composition and wherein each wt % is based upon the total combined weight of the active ingredients and the inert non-toxic carrier.

6. The composition as in claim 5, wherein said active ingredients in said composition comprise:
   25–500 Mg of Ma Huang;
   10–400 Mg of charcoal; and
   5–200 Mg of Vitamin B-6.

7. The composition as in claim 5, wherein said active ingredients in said composition comprise:
   167 Mg of Ma Huang;
   100 Mg of Charcoal; and
   25 Mg of Vitamin B-6.

8. The composition as in claim 5, wherein said active ts in said composition comprise:
   334 Mg of Ma Huang;
   200 Mg of charcoal; and
   50 Mg of Vitamin B-6.

9. A composition for relieving the side effects of alcohol on in humans comprising:
   a) set of inert, non toxic components; and
   b) a set of active components comprising:
      i) Ephedra;
      ii) Vitamin B-6; and
      iii) charcoal wherein said charcoal, Vitamin B-6, and Ephedra are in a weight ratio of approximately 1:2.5:10.

10. A composition for relieving the side effects of alcohol consumption in a human user comprising:
    a) a combination of inert, non toxic ingredients; and
    b) a combination of active ingredients comprising:
       i) at least about 1 mg of Ephedra;
       ii) at least about 1 mg of Vitamin B-6; and
       iii) at least about 1 mg of activated charcoal wherein said active ingredients and said inert, non toxic ingredients combine to provide an effective dosage for administering to the user.

11. The composition as in claim 10, wherein said active ingredients in said composition comprise at least about 1 Mg of Ephedra to 20 Mg of Ephedra, at least about 1 Mg of Vitamin B-6 to 50 Mg of Vitamin B-6, at least about 1 Mg of activated charcoal to 200 Mg of activated charcoal.

12. The composition as in claim 10, wherein said inert, non toxic ingredients comprise at least 1 Mg of Elcema G-250 powder Cellulose for Binding, at least about 1 Mg of Captex 300, at least about 1 Mg of Magnesium Stearate, and at least about 1 Mg of Sipernat 50 S mineral oil lubricant.

13. The composition as in claim 10, wherein said composition is administered in a capsule form.

* * * * *